(12) United States Patent
Govari et al.

(10) Patent No.: US 10,128,594 B2
(45) Date of Patent: Nov. 13, 2018

(54) CONNECTORS HAVING THREE-DIMENSIONAL SURFACES

(71) Applicant: BIOSENSE WEBSTER (ISRAEL) LTD., Yokneam (IL)

(72) Inventors: Assaf Govari, Haifa (IL); Andres Claudio Altmann, Haifa (IL); Yehuda Algawi, Binyamina-Givat Ada (IL); Mikhael Feldchtein, Kiryat Yam (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 362 days.

(21) Appl. No.: 14/978,479

(22) Filed: Dec. 22, 2015

(65) Prior Publication Data

US 2017/0172652 A1    Jun. 22, 2017

(51) Int. Cl.
| | |
|---|---|
| *H01R 12/71* | (2011.01) |
| *H01R 24/58* | (2011.01) |
| *A61B 18/14* | (2006.01) |
| *H01R 13/62* | (2006.01) |
| *H01R 13/627* | (2006.01) |
| *H01R 13/645* | (2006.01) |
| *H01R 24/68* | (2011.01) |
| *H01R 43/20* | (2006.01) |
| *A61B 18/00* | (2006.01) |

(52) U.S. Cl.
CPC ....... *H01R 12/714* (2013.01); *A61B 18/1492* (2013.01); *H01R 13/6205* (2013.01); *H01R 13/6273* (2013.01); *H01R 13/6456* (2013.01); *H01R 24/58* (2013.01); *H01R 24/68* (2013.01); *H01R 43/205* (2013.01); *A61B 2018/00178* (2013.01); *H01R 2201/12* (2013.01)

(58) Field of Classification Search
CPC .......................... H01R 43/205; H01R 12/714
See application file for complete search history.

(56) References Cited

U.S. PATENT DOCUMENTS

| | | | | |
|---|---|---|---|---|
| 3,060,417 A | * | 10/1962 | Blake ................... | B64D 45/02 340/508 |
| 4,373,764 A | * | 2/1983 | Ulrich ................... | H01R 12/85 29/854 |
| 4,376,927 A | * | 3/1983 | McGalliard .......... | H01H 85/046 174/254 |
| 4,714,437 A | | 12/1987 | Dyki | |
| 6,162,065 A | * | 12/2000 | Benham ................ | H01R 12/79 439/493 |
| 6,641,406 B1 | | 11/2003 | Yatskov et al. | |

(Continued)

FOREIGN PATENT DOCUMENTS

| | | |
|---|---|---|
| DE | 102013014750 A1 | 3/2015 |
| WO | 2006007421 A2 | 1/2006 |

OTHER PUBLICATIONS

European Patent Office, Extended Search Report of Application Serial No. 16205671.7, dated Apr. 12, 2017.

*Primary Examiner* — James Harvey

(57) ABSTRACT

Apparatus and methods are described, including apparatus that includes a connector. The connector includes a connector body including at least one mating surface having a first longitudinal end, and a second longitudinal end that is narrower than the first longitudinal end. A plurality of electrically-conductive terminals are coupled to the mating surface of the connector body. Other embodiments are also described.

16 Claims, 11 Drawing Sheets

(56) References Cited

U.S. PATENT DOCUMENTS

| | | | |
|---|---|---|---|
| 7,261,580 B1* | 8/2007 | Secora | H01R 12/83 |
| | | | 439/341 |
| 7,527,512 B2 | 5/2009 | Montena | |
| 7,934,954 B1 | 5/2011 | Chawgo et al. | |
| 8,162,683 B2 | 4/2012 | Loke et al. | |
| 8,784,138 B2* | 7/2014 | Shih | H01R 24/58 |
| | | | 439/668 |
| 8,821,194 B2* | 9/2014 | Shih | H01R 13/518 |
| | | | 439/668 |
| 9,017,092 B1* | 4/2015 | McCracken | H01R 13/62 |
| | | | 439/374 |
| 9,203,184 B1 | 12/2015 | Hui | |
| 9,314,208 B1* | 4/2016 | Altmann | A61B 5/6858 |
| 2001/0055906 A1 | 12/2001 | Morlesin | |
| 2004/0053532 A1* | 3/2004 | Jones | H01R 4/242 |
| | | | 439/581 |
| 2004/0058565 A1* | 3/2004 | Norland | H01R 12/62 |
| | | | 439/67 |
| 2006/0007421 A1 | 1/2006 | Flagello et al. | |
| 2007/0167089 A1 | 7/2007 | Gobron et al. | |
| 2011/0081788 A1* | 4/2011 | Robb | G02B 6/3604 |
| | | | 439/8 |
| 2013/0244453 A1* | 9/2013 | Sakamoto | H01R 12/53 |
| | | | 439/55 |
| 2014/0179170 A1 | 6/2014 | De Jong et al. | |
| 2015/0094713 A1* | 4/2015 | Pham | H01R 13/6205 |
| | | | 606/41 |
| 2017/0063005 A1* | 3/2017 | Wang | G02B 6/3684 |
| 2017/0082655 A1* | 3/2017 | Rosenberg | G01R 1/0416 |
| 2017/0172652 A1* | 6/2017 | Govari | A61B 18/1492 |
| 2017/0179631 A1* | 6/2017 | Feldchtein | H01R 13/44 |

* cited by examiner

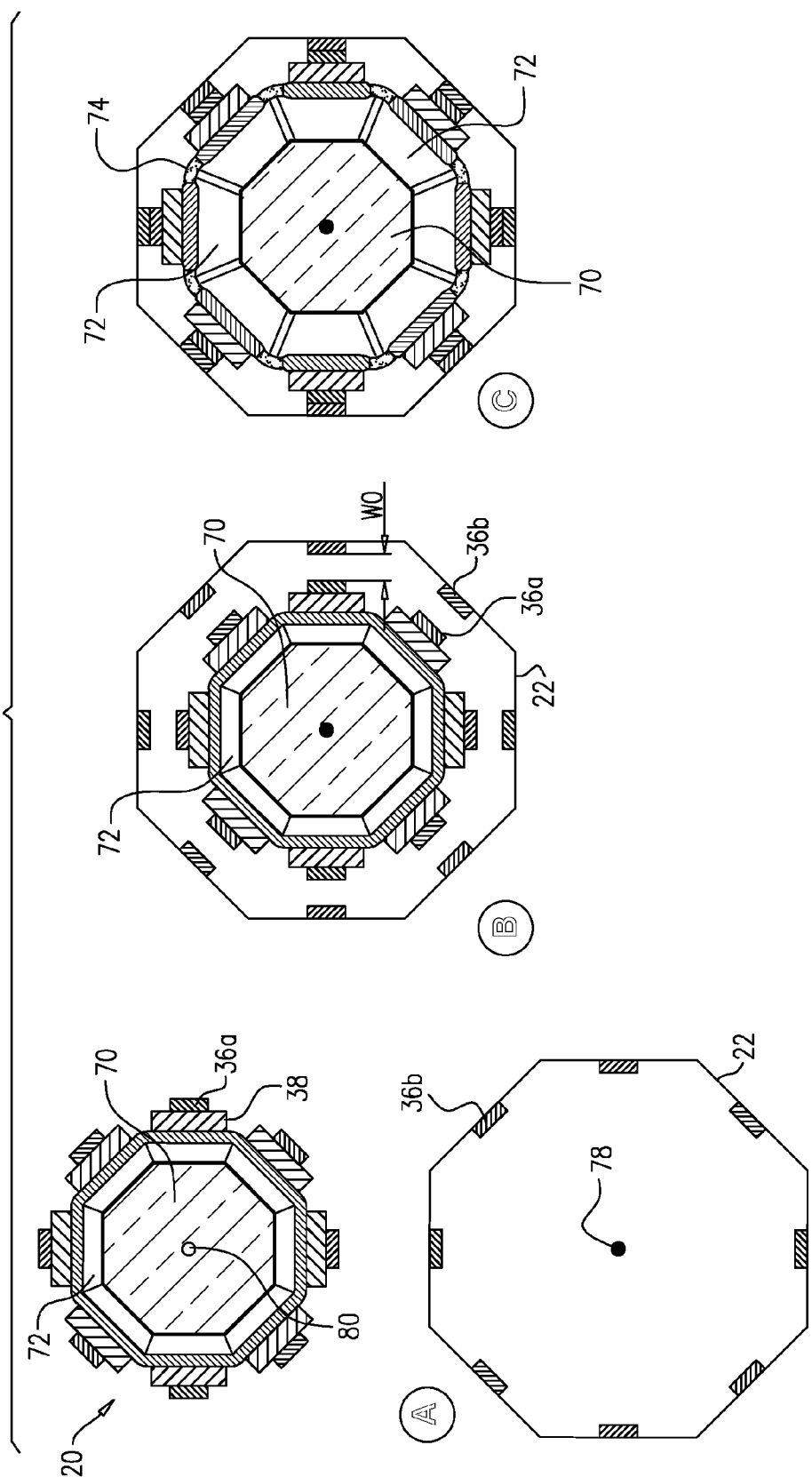

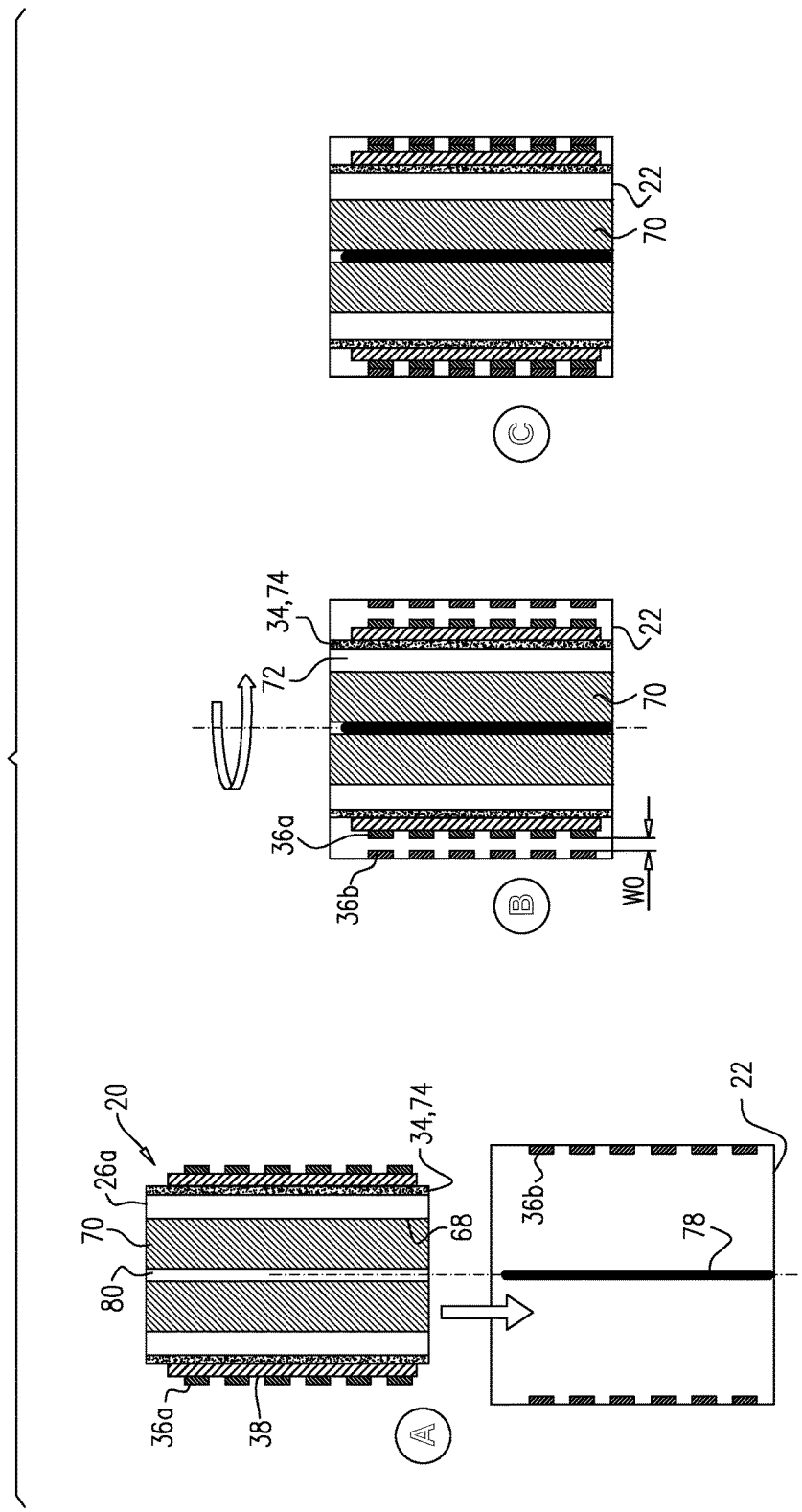

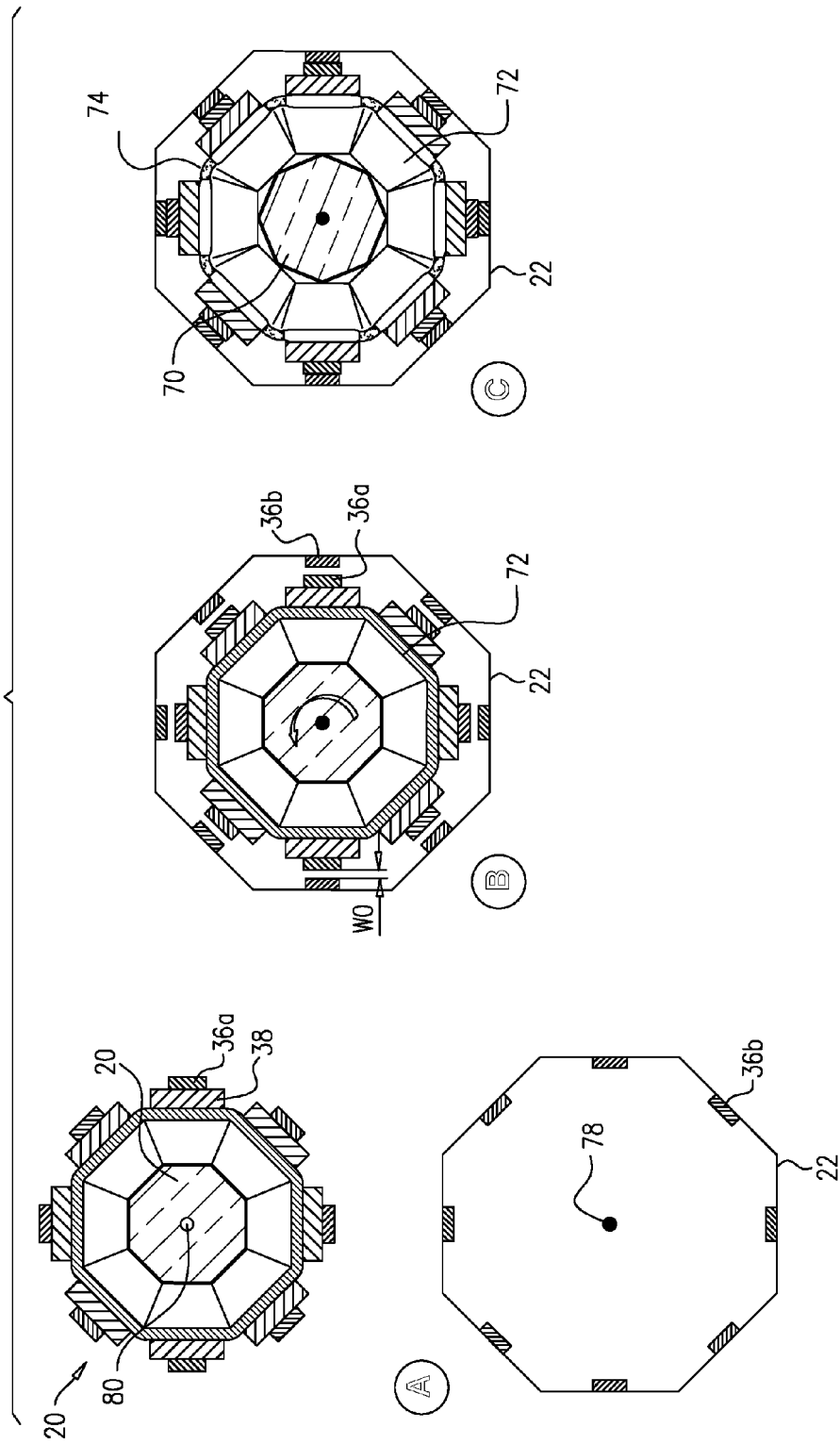

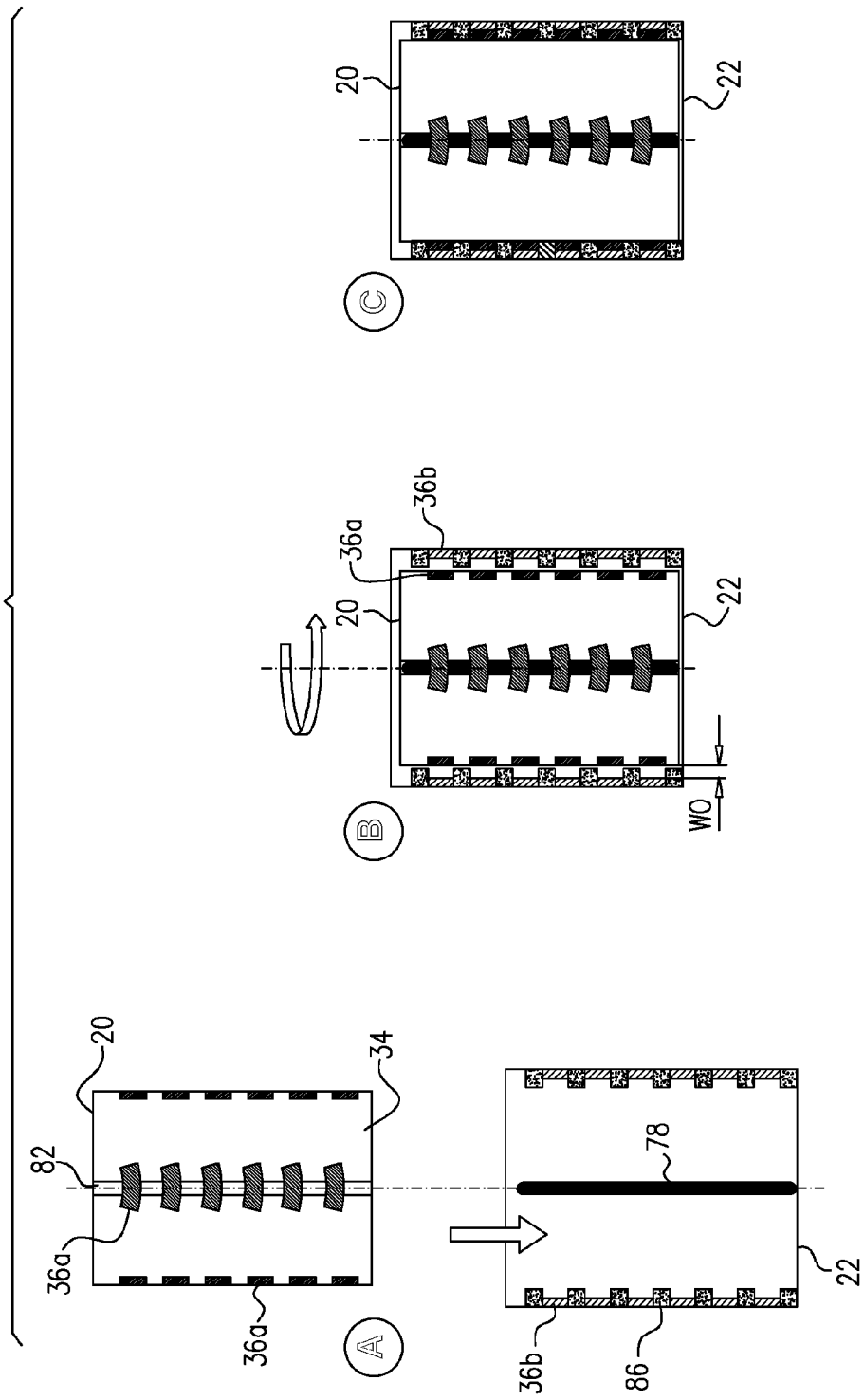

CONNECTORS HAVING THREE-DIMENSIONAL SURFACES

CROSS-REFERENCE TO RELATED APPLICATIONS

The present application is related to a U.S. patent application entitled "Preventing unwanted contact between terminals", U.S. application Ser. No. 14/978,644, filed on even date herewith.

FIELD OF THE INVENTION

The present invention relates to electrical connectors, e.g., for use in medical applications.

BACKGROUND

In some applications, a catheter having multiple electrodes at its distal end is used to sense and/or ablate cardiac tissue. In such applications, sufficient wiring needs to be provided for the passage of electrical signals between the proximal and distal ends of the catheter.

US Patent Publication 2001/0055906 to Morlesin, whose disclosure is incorporated herein by reference, describes a flexible medium voltage interconnection adapted to electrically interconnect receiving connectors of "bushings" of equipment stations. The interconnection comprises a conductive core including a metal conductor with, at each end thereof, an electrical connector adapted to mate the receiving connector of the bushing, and a flexible tube having at least an insulating layer of elastomeric material and covering the whole conductive core. The elastomeric material of the tube is preferably a synthetic terpolymer of ethylene, propylene and diene [EPDM] to increase the flexibility of the whole. In the method, the tube is expanded over the metal core of which the ends are foreseen with locking rings mating grooves of the tube in order to prevent a relative movement of the core with respect to the tube.

US Patent Publication 2007/0167089 to Gobron, whose disclosure is incorporated herein by reference, describes an electrical connector for providing a watertight electrical connection between a flat, single or multi-traced, rigid and/or flexible printed circuit and a separate electronics unit. The electrical connector is comprised of a plug having one or more keyhole-shaped slots which serve to mechanically secure the connection between the one or more traces of the circuit and one or more fixed pins on the body of the separate electronics unit. The plug is placed over the one or more pins such that the pins are inserted up through the wider portion of the slots and in a push or pull action, the pins are slid into the narrower portion of the slot such that the pins are locked into place. The conductive traces are then secured into contact with the electrical contacts of the separate electronics device.

U.S. Pat. No. 6,641,406 to Yatskov, whose disclosure is incorporated herein by reference, describes a flexible connector for high density circuit applications, comprising a multilayer flexible substrate upon which are formed a plurality of contact pads, in a density required by a particular application. This density may exceed two hundred contact pads per square inch. Contact pads of similar size and configuration are formed on the surface of another device, i.e., circuit board, and provision made to align the contact pads of the connector with those of the circuit board. Micro-pads are formed on the surface of the contact pads on the connector such, that when the connector is brought into contact with the circuit board, and sufficient pressure is applied, the micro-pads make actual electrical contact with the pads of the circuit board. Since the total surface area in contact, namely the sum of the surface areas of the micro-pads, is a small fraction of the total area of the connector, a large pressure is provided at the electrical contact interface even when low pressure is provided to the connector as a whole.

U.S. Pat. No. 4,714,437, whose disclosure is incorporated herein by reference, describes a separable electrical connector for a plurality of axially connectable cylindrical electrical terminals adapted for coupling to the threads of insulated wires and having an annular external recess on each of the terminals. The connector include an elongated, rigid, non-conductive, generally tubular member having a plurality of apertures extending axially therethrough and a plurality of outboard ramping retention abutments formed integrally with the tubular member upon at least one inner surface of a radially outboard portion of the tubular member. A plurality of axially extending terminal guide fingers is included upon a central land located within the tubular member. A spacer engages with the central land for displacing the terminal guide fingers in the direction of the ramping retention abutments so that the terminals will be retained securely within the connector assembly.

U.S. Pat. No. 8,162,683, whose disclosure is incorporated herein by reference, describes a miniature electrical connector comprising a floating and vertically orientable spring contact within but not physically secured to an electrically-conductive connector block of a female connector wherein the spring contact and connector block are designed such that the spring contact is vertically oriented and outwardly expanded when a male connector is inserted into the female connector to provide a conductive path between a male contact of the male connector and the connector block of the female connector.

U.S. Pat. No. 7,934,954, whose disclosure is incorporated herein by reference, describes, in one example embodiment, a coaxial cable connector for terminating a coaxial cable. The coaxial cable includes an inner conductor, an insulating layer, an outer conductor, and a jacket. The coaxial cable connector includes an internal connector structure, an external connector structure, and a conductive pin. The external connector structure cooperates with the internal connector structure to define a cylindrical gap that is configured to receive an increased-diameter cylindrical section of the outer conductor. The external connector structure is configured to be clamped around the increased-diameter cylindrical section so as to radially compress the increased-diameter cylindrical section between the external connector structure and the internal connector structure. The conductive pin is configured to deform the inner conductor.

U.S. Pat. No. 7,527,512, whose disclosure is incorporated herein by reference, describes an expanding contact used within a cable connector to make a solid connection with a hollow center conductor of a coaxial cable and that includes two pieces, a pin and a guide. The pin includes a plurality of slots which form a like plurality of fingers, while the guide includes a plurality of tabs which fit into the plurality of slots. Ends of the fingers include a ramped portion which interacts with a ramped portion of the guide. When the pin is pushed against the guide, the fingers are pushed outward because of the ramped portions of the fingers sliding against the ramped portion of the guide. Before the ends are pushed outward, the pin/guide combination can slide easily into and out of the hollow center conductor, but when the fingers are pushed outward, the fingers make a substantial interference fit with the inner walls of the hollow center conductor.

SUMMARY OF THE INVENTION

There is provided, in accordance with some embodiments of the present invention, apparatus that includes a connector. The connector includes a connector body that includes at least one mating surface having a first longitudinal end, and a second longitudinal end that is narrower than the first longitudinal end. A plurality of electrically-conductive terminals are coupled to the mating surface of the connector body.

In some embodiments, the mating surface is an inner surface of the connector body, such that the connector body is a female-connector body.

In some embodiments,
the female-connector body is shaped to define at least one protrusion that protrudes from the second longitudinal end of the female-connector body toward the first longitudinal end of the female-connector body, the protrusion not being at a transverse center of the female-connector body.

In some embodiments, the protrusion does not contact the inner surface of the female-connector body.

In some embodiments, the apparatus further includes:
an electrically-insulative layer of material covering the inner surface of the connector body and shaped to define a plurality of apertures positioned such that each one of the apertures is aligned with a respective one of the electrically-conductive terminals; and
a plurality of electrical conductors disposed, respectively, within the apertures.

In some embodiments, the mating surface is an outer surface of the connector body, such that the connector body is a male-connector body, and the terminals are male-connector terminals.

In some embodiments, the second longitudinal end of the male-connector body is shaped to define at least one orifice that is not at a transverse center of the male-connector body.

In some embodiments, the orifice is completely enclosed by the second longitudinal end of the male-connector body.

In some embodiments, the apparatus further includes a female connector, including:
a female-connector body shaped to fittingly receive the male-connector body and the male-connector terminals, and
a plurality of electrically-conductive female-connector terminals coupled to an inner surface of the female-connector body, each of the female-connector terminals being positioned to contact a respective one of the male-connector terminals when the male-connector terminals are inside the female connector.

In some embodiments, the terminals include a plurality of pins.

In some embodiments, the terminals include a plurality of sockets.

In some embodiments, the terminals are terminals of one or more printed circuit boards (PCBs) coupled to the mating surface.

In some embodiments, the PCBs include, between at least one pair of the terminals, a spacing element that is level with the pair of terminals.

In some embodiments, the mating surface is conically-shaped.

In some embodiments, the electrically-conductive terminals consist of 100-500 terminals.

In some embodiments, the electrically-conductive terminals consist of 500-700 terminals.

In some embodiments, the apparatus further includes a compressible layer of material between at least a portion of the connector body and the terminals.

In some embodiments, the layer of material includes a material selected from the group consisting of: polyester, microcellular urethane, and silicone.

In some embodiments, the layer of material is over-molded onto the connector body.

In some embodiments, the apparatus is shaped to define one or more ridges configured to facilitate a fastening of the apparatus to a complementary connector in a mating position, by receiving one or more fasteners of the complementary connector.

In some embodiments, the apparatus further includes one or more fasteners configured to fasten the apparatus to a complementary connector in a mating position.

In some embodiments, the fasteners include one or more tabs.

In some embodiments, the fasteners include one or more magnets.

In some embodiments, the apparatus further includes a catheter, the connector body being disposed at a proximal end of the catheter.

In some embodiments, the connector body is disposed inside the catheter.

In some embodiments, the catheter includes a plurality of electrodes at a distal end thereof, each of the electrodes at the distal end of the catheter being connected to a respective one of the terminals.

In some embodiments, the apparatus further includes:
an electrically-insulative connector sheath, shaped to define a plurality of apertures positioned such that, when one of the connector body and connector sheath is inside the other one of the connector body and connector sheath, each one of the apertures is aligned with a respective one of the electrically-conductive terminals; and
a plurality of electrical conductors disposed, respectively, within the apertures.

In some embodiments, the plurality of electrical conductors include a plurality of electrically-conductive balls.

There is further provided, in accordance with some embodiments of the present invention, a method for establishing an electrical connection between a male connector, which includes a plurality of electrically-conductive male-connector terminals, and a female connector, which includes a plurality of electrically-conductive female-connector terminals. The method includes providing an electrically-insulative connector sheath shaped to define a plurality of apertures, a plurality of electrical conductors being disposed, respectively, within the apertures. By inserting a connector body of the male connector into the connector sheath, the electrical conductors are pushed toward the female-connector terminals, until each one of the electrical conductors is in contact with both a respective one of the male-connector terminals and a respective one of the female-connector terminals.

In some embodiments, the method further includes, prior to inserting the connector body into the connector sheath, inserting the connector sheath into the female connector.

There is further provided, in accordance with some embodiments of the present invention, a connector. The connector includes a connector body having a first longitudinal end and a second longitudinal end. The connector further includes a compressible layer of material coupled to the connector body, between the first and second longitudinal ends of the connector body, and a plurality of electrically-conductive terminals coupled to the layer of material.

There is further provided, in accordance with some embodiments of the present invention, a method of manufacture. The method includes providing a connector body including at least one mating surface having a first longitudinal end, and a second longitudinal end that is narrower than the first longitudinal end, and coupling a plurality of electrically-conductive terminals to the mating surface.

There is further provided, in accordance with some embodiments of the present invention, a connector. The connector includes a connector body that includes at least one mating surface, at least a portion of which is oriented at an oblique angle with respect to a central longitudinal axis of the connector body. A plurality of electrically-conductive terminals are coupled to the mating surface of the connector body.

There is further provided, in accordance with some embodiments of the present invention, connector apparatus. The apparatus includes a male-connector body including at least one mating surface, and shaped to define a hollow core. A plurality of electrically-conductive male-connector terminals are coupled to the mating surface of the male-connector body. A longitudinal insert is configured to, by moving inside the hollow core, push the male-connector terminals radially outward.

In some embodiments, the male-connector terminals are coupled to the mating surface of the male-connector body in a longitudinal and circumferential arrangement.

In some embodiments, the longitudinal insert is configured to push the male-connector terminals by moving distally inside the hollow core.

In some embodiments, a distal end of the hollow core is narrower than a proximal end of the hollow core.

In some embodiments, a distal end of the longitudinal insert is narrower than a proximal end of the longitudinal insert.

In some embodiments, an outer surface of the longitudinal insert is pyramidally-shaped.

In some embodiments, an outer surface of the longitudinal insert is conically-shaped.

In some embodiments, the longitudinal insert is configured to push the male-connector terminals by rotating with respect to the hollow core.

In some embodiments, the longitudinal insert is polygonal-prism-shaped.

In some embodiments, the apparatus further includes a female connector configured to matingly receive the male-connector body.

In some embodiments, the female connector includes a longitudinal protrusion, and the insert is shaped to define a hollow insert-core shaped to fittingly receive the protrusion.

In some embodiments, the male-connector body is insertable into the female connector such that there is gap of at least one mm between each of the male-connector terminals and its nearest female-connector terminal.

In some embodiments, the mating surface is polygonal-prism-shaped.

In some embodiments, the mating surface is cylindrically-shaped.

In some embodiments, the mating surface includes an elastic material, configured to facilitate the pushing of the male-connector terminals by circumferentially expanding.

There is further provided, in accordance with some embodiments of the present invention, a method for establishing an electrical connection between a male connector, which includes a plurality of electrically-conductive male-connector terminals arranged both longitudinally and circumferentially, and a female connector, which includes a plurality of electrically-conductive female-connector terminals arranged both longitudinally and circumferentially. The male connector is inserted into the female connector, such that no one of the male-connector terminals is in contact with any one of the female-connector terminals. Subsequently, each one of the male-connector terminals is brought into contact with a respective one of the female-connector terminals.

In some embodiments, inserting the male connector into the female connector includes fully inserting the male connector into the female connector.

In some embodiments, bringing each one of the male-connector terminals into contact with a respective one of the female-connector terminals includes bringing each one of the male-connector terminals into contact with a respective one of the female-connector terminals by rotating the male connector and female connector with respect to one another.

There is further provided, in accordance with some embodiments of the present invention, connector apparatus. The apparatus includes a male-connector body including at least one mating surface, and a plurality of electrically-conductive male-connector terminals coupled to the mating surface of the male-connector body, the male-connector terminals being radially movable with respect to the male-connector body.

In some embodiments, the male-connector terminals are radially movable with respect to the male-connector body by virtue of being compressible.

In some embodiments, the male-connector terminals are coupled to the mating surface of the male-connector body in a longitudinal and circumferential arrangement.

In some embodiments, the apparatus further includes a female connector including a plurality of electrically-conductive female-connector terminals coupled to an inner surface of the female connector, the female connector being configured to matingly receive the male-connector body.

In some embodiments, the inner surface of the female connector includes a plurality of electrically-insulative protrusions that longitudinally separate between the female-connector terminals.

The present invention will be more fully understood from the following detailed description of embodiments thereof, taken together with the drawings, in which:

BRIEF DESCRIPTION OF THE DRAWINGS

FIGS. 5, 6A-B, 7A-B, and 8A-B are schematic illustrations of connectors that facilitate the prevention of unwanted contact between terminals, in accordance with some embodiments of the present invention.

DETAILED DESCRIPTION OF EMBODIMENTS

Overview

Figure 1:
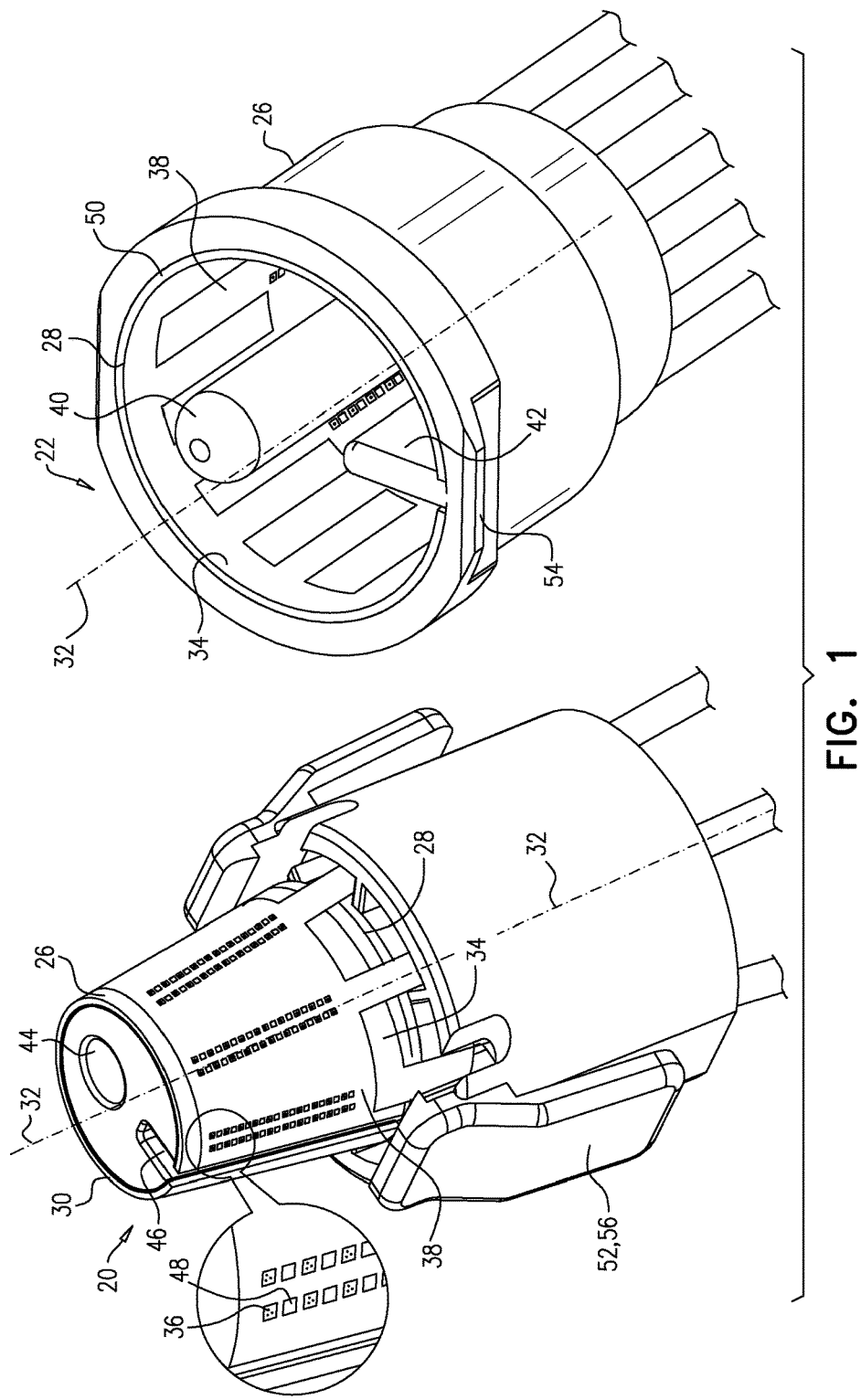
FIGS. 1-3 are schematic illustrations of a male connector and a female connector, in accordance with some embodiments of the present invention.

A catheter having multiple electrodes at its distal end typically requires multiple connecting wires terminating in respective connectors at a proximal end of the catheter. Some catheters, e.g., "basket" catheters, may have upwards of 100 electrodes, and correspondingly a relatively large number of connecting wires.

One possibility is to have the wires terminate in a single, two-dimensional rectilinear arrangement of sockets in a female connector at the proximal end of the catheter, the sockets mating with pins of a corresponding male connector (or vice versa). To accommodate the large number of pins and sockets needed, however, the male and female connectors may need to be undesirably large in one or both of the two dimensions. Although it may be possible to densely pack the pins and sockets, such a solution may be relatively expensive.

Embodiments of the present invention accommodate the large number of connecting wires by providing a conically-shaped, or otherwise suitably-shaped, connector. A plurality of electrically-conductive connecting terminals are coupled to at least one mating surface of the connector between the longitudinal ends of the connector. For example, for a female connector, the terminals are coupled to an inside surface of the connector. Such a configuration advantageously utilizes a third, longitudinal dimension of the connector that is not utilized in the above-described single, two-dimensional rectilinear arrangement. Thus, a relatively large number of terminals may be coupled to the connector, without overly increasing the length of the connector in any dimension, and without needing to pack the terminals too densely. For example, in some embodiments, the connector may comprise more than 100 (e.g., 100-500), or even more than 500 (e.g., 500-700) terminals.

In some embodiments, flexible printed circuit boards (PCBs) are coupled to the mating surface of the connector, and terminals on the PCBs are used as the connecting terminals. In some embodiments, a compressible layer of material is coupled to the connector body, underneath the PCBs. The compressible layer of material pushes the PCBs away from the connector, towards the complementary connector, thus improving the contact between the respective sets of terminals.

Some connectors described herein are configured to largely prevent any unwanted contact between the terminals as the male connector is in the process of being inserted into the female connector. For example, in some embodiments, an electrically-insulative connector sheath inhibits contact between the terminals, until the male connector is fully inserted into (and correctly oriented with respect to) the female connector. In other embodiments, the connectors are shaped and/or sized to allow full insertion of the male connector into the female connector without any contact between the terminals. Only upon the male connector being fully inserted, are the terminals of the male connector brought into contact with the terminals of the female connector.

Apparatus Description

Reference is initially made to FIG. 1, which is a schematic illustration of a male connector 20 and a female connector 22, in accordance with some embodiments of the present invention.

Each one of the connectors comprises a connector body 26 comprising at least one mating surface 34, having a first longitudinal end 28, and a second longitudinal end 30 that is narrower than first longitudinal end 28. For example, as shown in FIG. 1, surface 34 may be conically-shaped, i.e., shaped to define at least a portion of a cone. For each of the connectors, a plurality of electrically-conductive terminals 36 are coupled to surface 34, between the first and second longitudinal ends of the connector body. The respective shapes of the connector bodies are complementary, such that the female-connector body is shaped to fittingly receive the male connector.

The respective surfaces 34 are referred to herein as "mating surfaces," in that the connectors mate with one another by the terminals on one of the mating surfaces contacting the terminals on the other one of the mating surfaces. Connector 22 is referred to herein as a female connector, in that the terminals of connector 22 are coupled to an inner surface of the body of connector 22; in other words, the mating surface of connector 22 is an inner surface of the connector. Conversely, connector 20 is referred to herein as a male connector, in that the terminals of connector 20 are coupled to an outer surface of the body of connector 20; in other words, the mating surface of connector 20 is an outer surface of the connector. Each of the female-connector terminals is positioned to contact a respective one of the male-connector terminals, when the male connector is inside the female connector.

It is noted that the scope of the present invention includes connector bodies comprising a mating surface of any suitable shape, in addition to the conical shape shown in FIG. 1. In general, a suitable shape is a shape that (i) is narrower at one of its longitudinal ends than at the other one of its longitudinal ends, and/or (ii) is oriented at an oblique angle with respect to the central longitudinal axis 32 of the connector body. Properties (i) and (ii) help the female-connector body fittingly receive the male connector, and/or provide three dimensions of surface area on which the connecting terminals may be disposed. For example, in some embodiments, a portion of the connector body may be shaped to define at least a portion of a pyramid (e.g., a triangular pyramid, a rectangular pyramid, such a square pyramid, or a pyramid having any other type of suitable polygonal base), such that the central longitudinal axis of the connector body runs between the base and apex of the pyramid. In such embodiments, the terminals may be coupled to one or more surfaces of the pyramid between the base and the apex, such that the one or more surfaces of the pyramid define one or more mating surfaces of the connector body.

(In the context of the claims and specification of the present disclosure, the term "longitudinal" refers to the direction passing between the proximal and distal ends of the element under discussion. For example, for the male connectors described herein, the distal end of the connector is the end of the connector that first enters the female connector upon mating, and the opposite, proximal end of the connector may be said to be longitudinally-separated from the distal end. The "central longitudinal axis" of an element is the set of all centroids of cross-sectional sections of the element, the cross-sectional sections being transverse to the longitudinal direction. The term "radial" refers to a direction toward or away from the central longitudinal axis, perpendicularly to the central longitudinal axis.)

Typically, terminals 36 belong to one (as in FIG. 1) or more PCBs 38 coupled to surface 34. PCBs 38 are typically relatively flexible, such that they conform to the mating surface of the connector body. PCBs 38 may be shaped to define the terminals, or the terminals may be attached (e.g., soldered) to the PCBs. In alternate embodiments, the terminals do not belong to PCBs. For example, in some embodiments, the terminals are painted or 3D-printed onto the mating surface of the connector body.

In some embodiments, at least one of the connectors comprises a compressible layer 50 of material between at least a portion of the connector body and the terminals.

Layer 50 provides a pushing force that facilitates contact between the complementary sets of terminals. Layer 50 may comprises, for example, polyester, microcellular urethane such as a PORON® microcellular urethane foam, or silicone. Layer 50 is typically over-molded onto the connector body.

Figure 2:
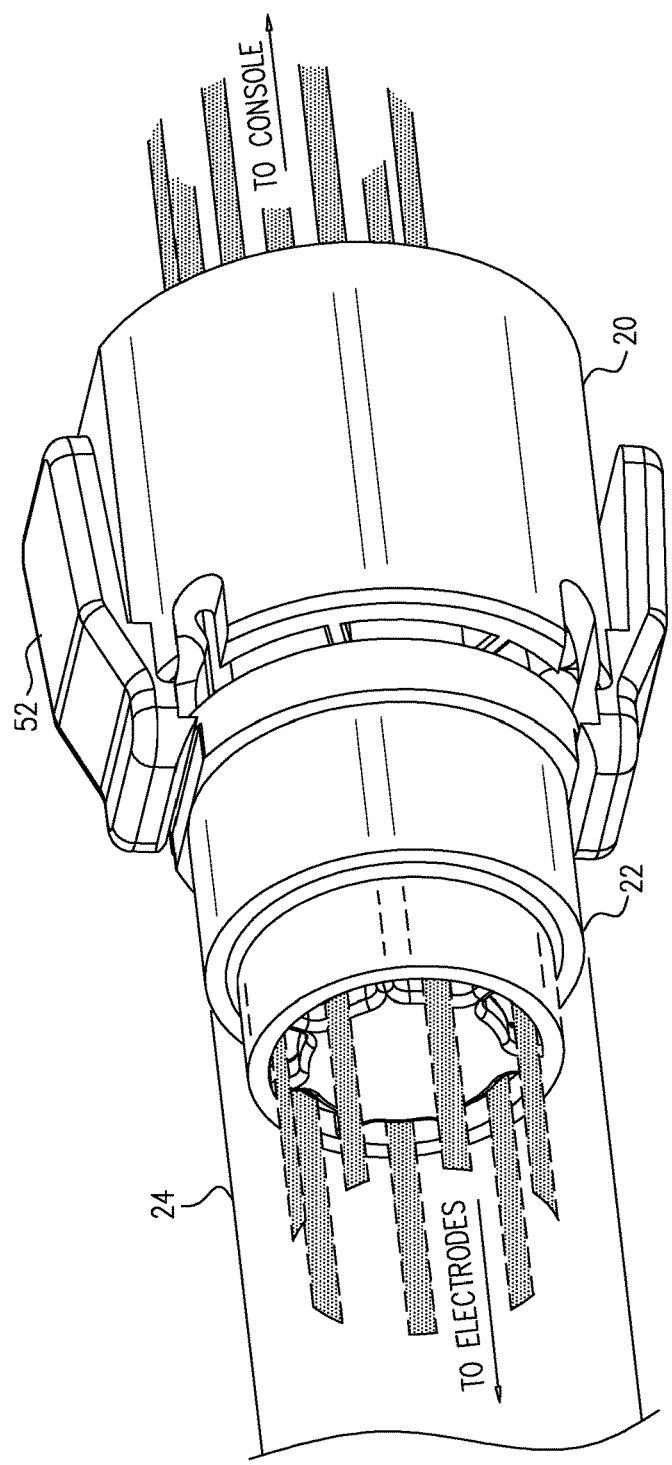

Reference is now additionally made to FIG. 2, which is a schematic illustration of male connector 20 and female connector 22 in a mating position, in accordance with some embodiments of the present invention. As shown in FIG. 2, in some embodiments, female connector 22 is disposed at the proximal end of a catheter 24, such as within, or partially within, catheter 24. As described above, catheter 24 may comprise a plurality of electrodes (not shown) at a distal end thereof, each of the electrodes being connected to a terminal on the female connector. For example, each of the electrodes may be connected to a respective one of the terminals. Alternatively, one or more of the terminals may be "shared" by multiple electrodes, using, for example, multiplexing techniques.

Each of the terminals on the male connector may be connected to, for example, a radiofrequency generator (for ablation) and/or an electrocardiogram monitor, e.g., disposed inside a console at the proximal end of the catheter.

In alternative embodiments, the male connector is disposed at the proximal end of the catheter, such as within, or partially within, the catheter, and the female connector is disposed outside the catheter.

In some embodiments, the female-connector body is shaped to define at least one protrusion that protrudes from second longitudinal end 30 of the female-connector body toward first longitudinal end 28 of the female-connector body. For example, FIG. 1 shows a first protrusion 40, which does not contact the inner surface of the female-connector body (i.e., the mating surface to which the terminals are coupled), and a second protrusion 42, which contacts the inner surface. In such embodiments, second longitudinal end 30 of the male connector is shaped to define at least one complementary orifice. For example, FIG. 1 shows a first orifice 44, which receives first protrusion 40, and a second orifice 46, which receives second protrusion 42. (First orifice 44 is completely enclosed by the second longitudinal end of the male-connector body, while second orifice 46 is not.)

The first protrusion is not at the transverse center of the female-connector body (and likewise, the first orifice is not at the transverse center of the male-connector body). Hence, the first protrusion and first orifice "break the symmetry" of the connectors, such that only one mating position is possible. In other words, the first protrusion and first orifice help the connectors be aligned such that each male-connector terminal comes into contact with the appropriate female-connector terminal. Moreover, first protrusion 40 helps prevent a finger from accidentally touching one of the female-connector terminals.

Second protrusion 42, along with second orifice 46, help prevent unwanted "jiggling" of the connectors (and hence, unwanted contact between the terminals), as the connectors are mated with one another. Second protrusion 42 and second orifice 46 also provide for proper alignment between the connectors, as described above for the first protrusion and first orifice. In some embodiments, second protrusion 42 and second orifice 46 also act as a "key" that prevents the wrong pair of connectors from being mated with one another.

Figure 3:
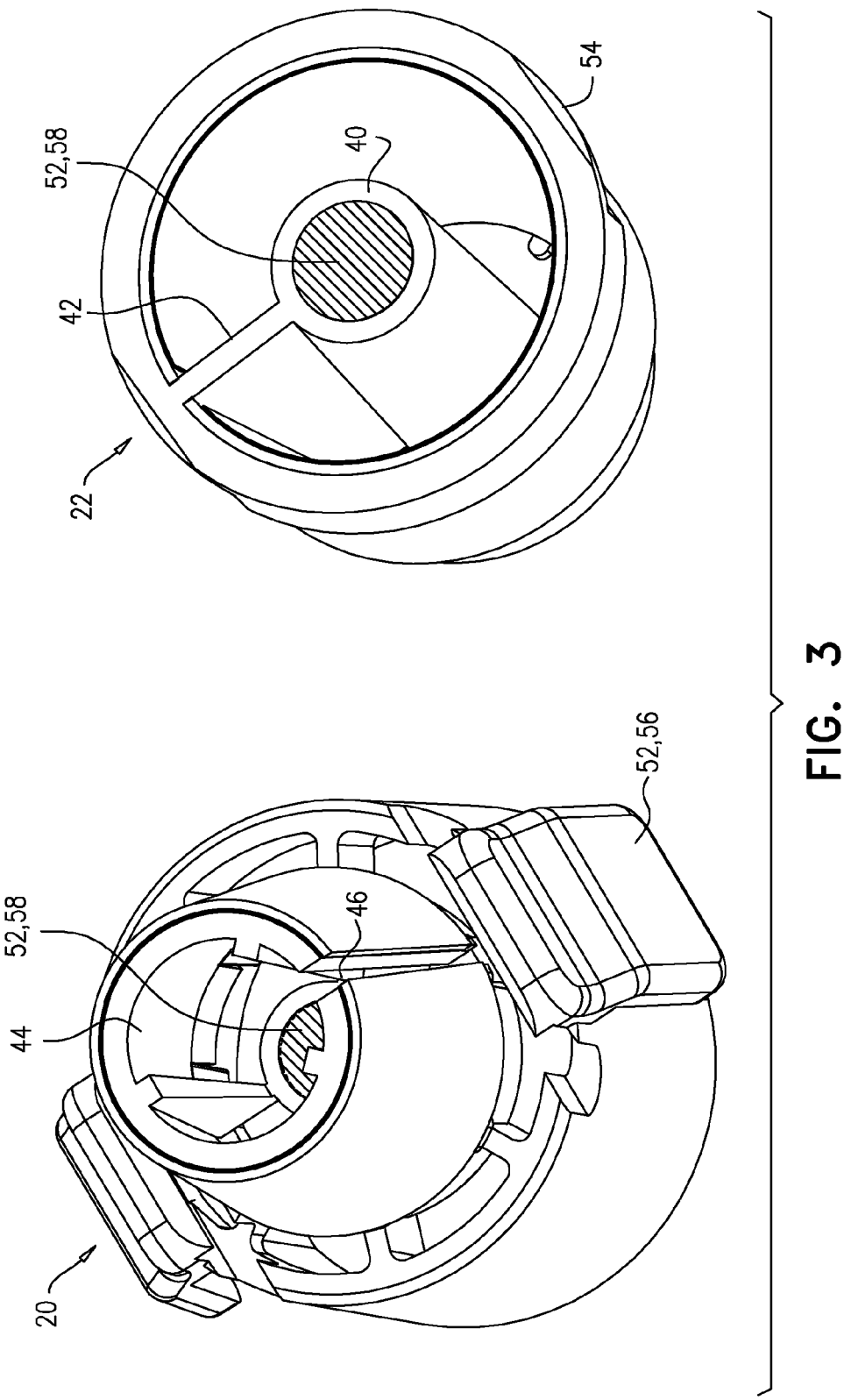

Reference is now additionally made to FIG. 3, which is a schematic illustration of male connector 20 and female connector 22, in accordance with some embodiments of the present invention. (For simplicity, FIG. 3 omits certain details, such as the PCBs and terminals shown in FIG. 1.)

In some embodiments, at least one of the connectors further comprises one or more fasteners 52, which fasten the connector to the complementary connector in a mating position. For example, as shown in FIGS. 1-3, one of the connectors (e.g., the male connector) may comprise tabs 56. In such embodiments, the other connector may be shaped to define one or more ridges 54, which receive the fasteners. Alternatively or additionally, at least one of the connectors may comprise magnets 58. For example, as shown in FIG. 3, each one of the connectors may comprise a respective magnet 58. The complementary magnets attracts one another, thus fastening the connectors with one another in a mating position.

Figure 4:
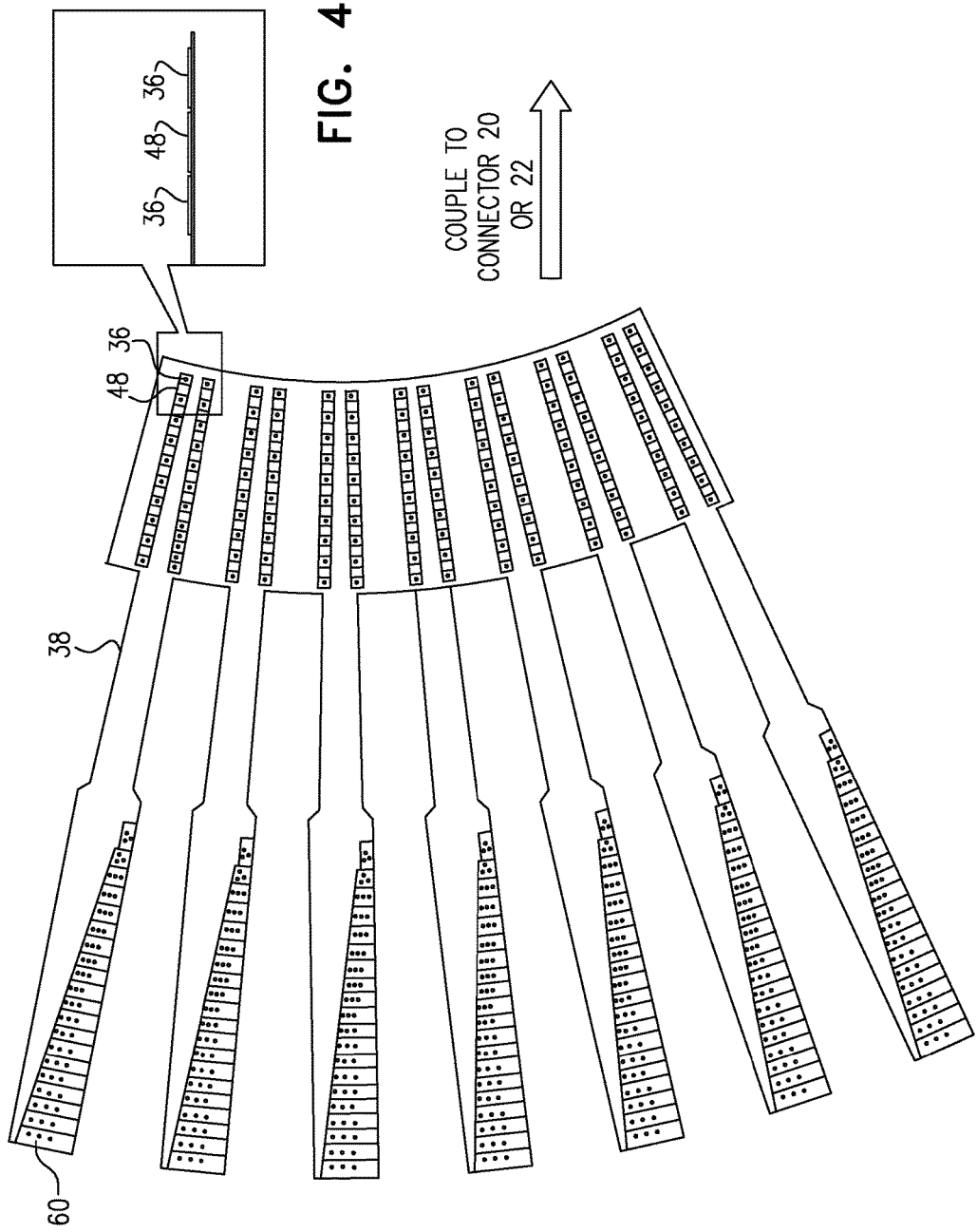
FIG. 4 is a schematic illustration of a PCB, in accordance with some embodiments of the present invention.

Reference is now made to FIG. 4, which is a schematic illustration of a PCB 38, in accordance with some embodiments of the present invention. In some embodiments, at least one of the PCBs comprises, between at least one pair of neighboring terminals, a spacing element 48 (also shown in FIG. 1) that is level with the pair of terminals, i.e., the spacing element protrudes the same distance from the PCB as do the terminals. (Typically, as shown in FIG. 4, there is a respective spacing element between each pair of neighboring terminals.) Spacing element 48 facilitates the mating of the connectors with one another, by filling up the space between the terminals that might otherwise "catch" a terminal of the complementary connector. In the particular embodiment shown in FIG. 4, the end of PCB 38 that is opposite the terminals comprises connecting elements 60, which facilitate the connection of the terminals to connecting wires that run to the electrodes, or to connecting wires that run to the radiofrequency generator, electrocardiogram monitor, and/or other apparatus at the proximal end of the catheter.

In some embodiments, at least some of the terminals on one of the connectors are pins, and at least some of the terminals on the other one of the connectors are sockets, shaped to receive the pins.

Reference is now made to FIGS. 5-8, which are schematic illustrations of connectors that facilitate the prevention of unwanted contact between the terminals as the male and female connectors are in the process of being inserted into one another, in accordance with some embodiments of the present invention. In general, the embodiments shown in FIGS. 5-8 may be combined with any relevant apparatus or technique described above. For example, fasteners 52 (FIGS. 1-3) may be used with the embodiments shown in FIGS. 5-8.

Figure 5:
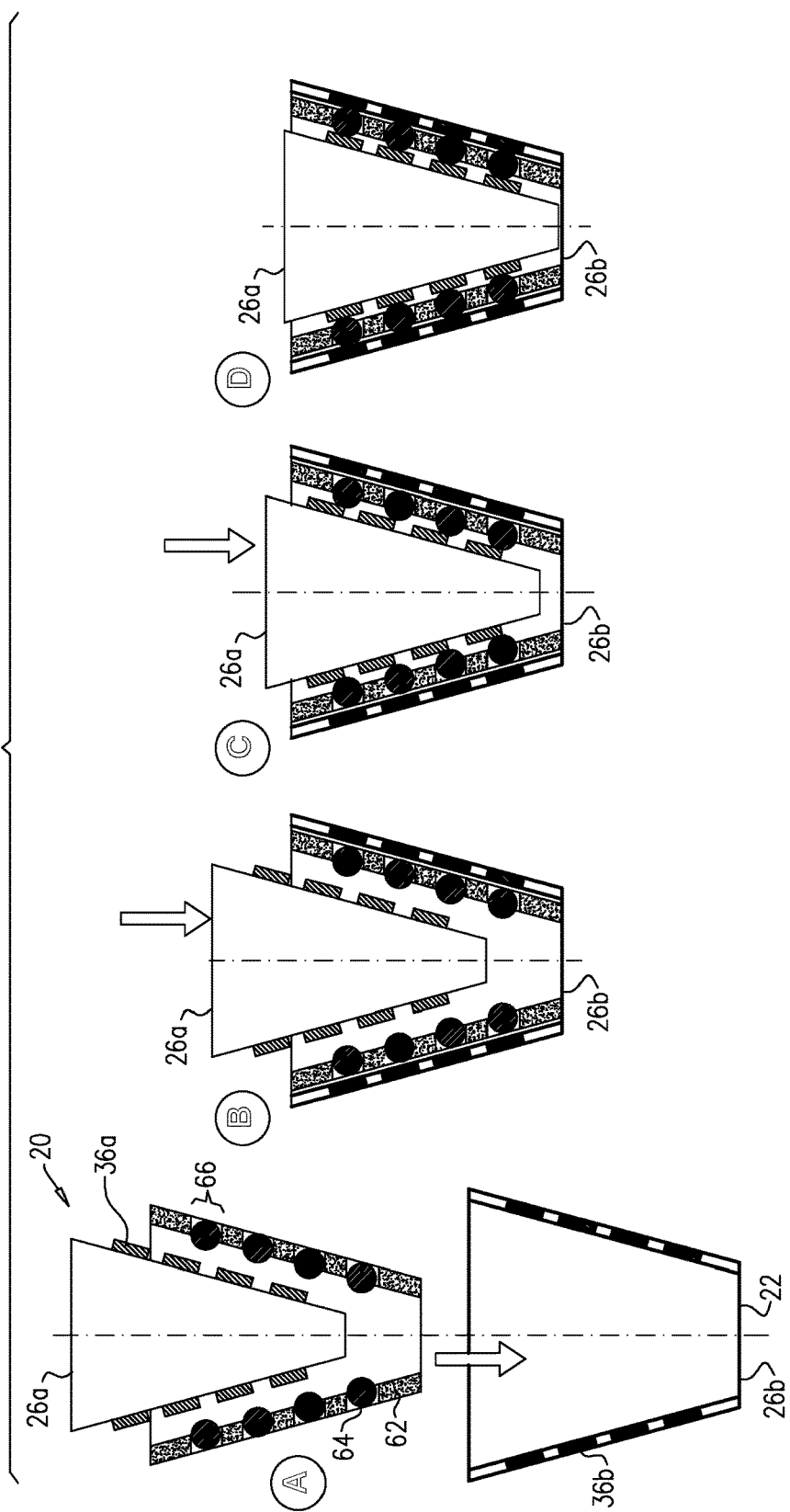

Reference is first made to FIG. 5, which shows an electrically-insulative connector sheath 62. As described immediately below, the prevention of unwanted contact between the terminals is facilitated by the interposition of connector sheath 62 between the male-connector body and the inside surface of the female-connector body. Although FIG. 5 shows connector sheath 62 used with the previously-described conically-shaped connectors, it is noted that the connector sheath may be used with connectors having any suitable shape.

As shown in FIG. 5, in some embodiments, connector sheath 62 is coupled to male-connector body 26a. (In such embodiments, despite being coupled together, the male-connector body and connector sheath are typically longitudinally movable with respect to one another, such that the male-connector body may be inserted into, and at least partly withdrawn from, the connector sheath.) In other embodiments (not shown), the connector sheath is coupled to the female-connector body, such that the connector sheath is disposed inside of the female-connector body. In yet other embodiments, connector sheath 62 is not coupled to either one of the connector bodies, but rather, is placed over the male-connector body, or inside the female-connector body, prior to the mating of the two connectors.

As shown in FIG. 5, the connector sheath is shaped to define a plurality of apertures 66. Apertures 66 are positioned such that, (i) when connector body 26a of the male connector is inside the connector sheath, each one of the apertures is aligned with a respective one of the terminals 36a of the male connector, and (ii) when the connector sheath is inside connector body 26b of the female connector, each one of the apertures is aligned with a respective one of the terminals 36b of the female connector. A plurality of electrical conductors 64, such as the electrically-conductive (e.g., metallic) balls shown in the figure, are disposed, respectively, within the apertures, i.e., a respective electrical conductor 64 is disposed within each one the apertures.

FIG. 5 illustrates the manner in which an electrical connection is established between the male connector and the female connector. In step A, the connector sheath is inserted into the female connector body, before the male connector body is fully inserted into the connector sheath. (As noted above, in alternate embodiments, the connector sheath is coupled to the female-connector body, such that there may be no need to insert the connector sheath into the female-connector body prior to each instance of establishing an electrical connection.) Subsequently, in step B, the male-connector body is inserted further into the connector sheath. As male-connector terminals 36a come into contact with electrical conductors 64 (step C), the male-connector terminals push the electrical conductors toward female-connector terminals 36b, until each one of the electrical conductors is in contact with both a respective one of the male-connector terminals and a respective one of the female-connector terminals (step D). Since the electrical conductors come into contact with the terminals only near the end of the insertion of the male connector (at steps C and D), at which point the male-connector terminals and female-connector terminals are properly aligned with respect to each other, unwanted contact between the terminals is largely avoided (e.g., entirely prevented).

In some embodiments (not shown), the sheath is a fully integrated part of the female connector. In such embodiments, the female connector comprises an electrically-insulative layer of material that covers the inner surface of the female-connector body and is shaped to define a plurality of apertures, inside of which the electrical conductors are disposed.

FIGS. 6A-B, 7A-B, and 8A-B show embodiments in which the connectors are configured to be mated with one another in two separate steps. In the first step, the male connector is inserted (typically, fully inserted) into the female connector. Due to the structure of the connectors (as described below), there is little or no chance of any contact between the terminals occurring during the insertion. Subsequently, in the second mating step, the male-connector terminals are brought into contact with the female-connector terminals.

In FIGS. 6A-B and 7A-B, the prevention of unwanted contact between the terminals during the insertion is facilitated by the radial difference in size between the connectors. In particular, the male-connector body is radially small enough, relative to the inside surface of the female connector, such that upon insertion of the male-connector body into the female connector, the two connectors are separated by a gap. Subsequently to the insertion, the male-connector body is radially expanded, thus pushing the male-connector terminals toward the female-connector terminals, until contact is established.

Figure 6A:
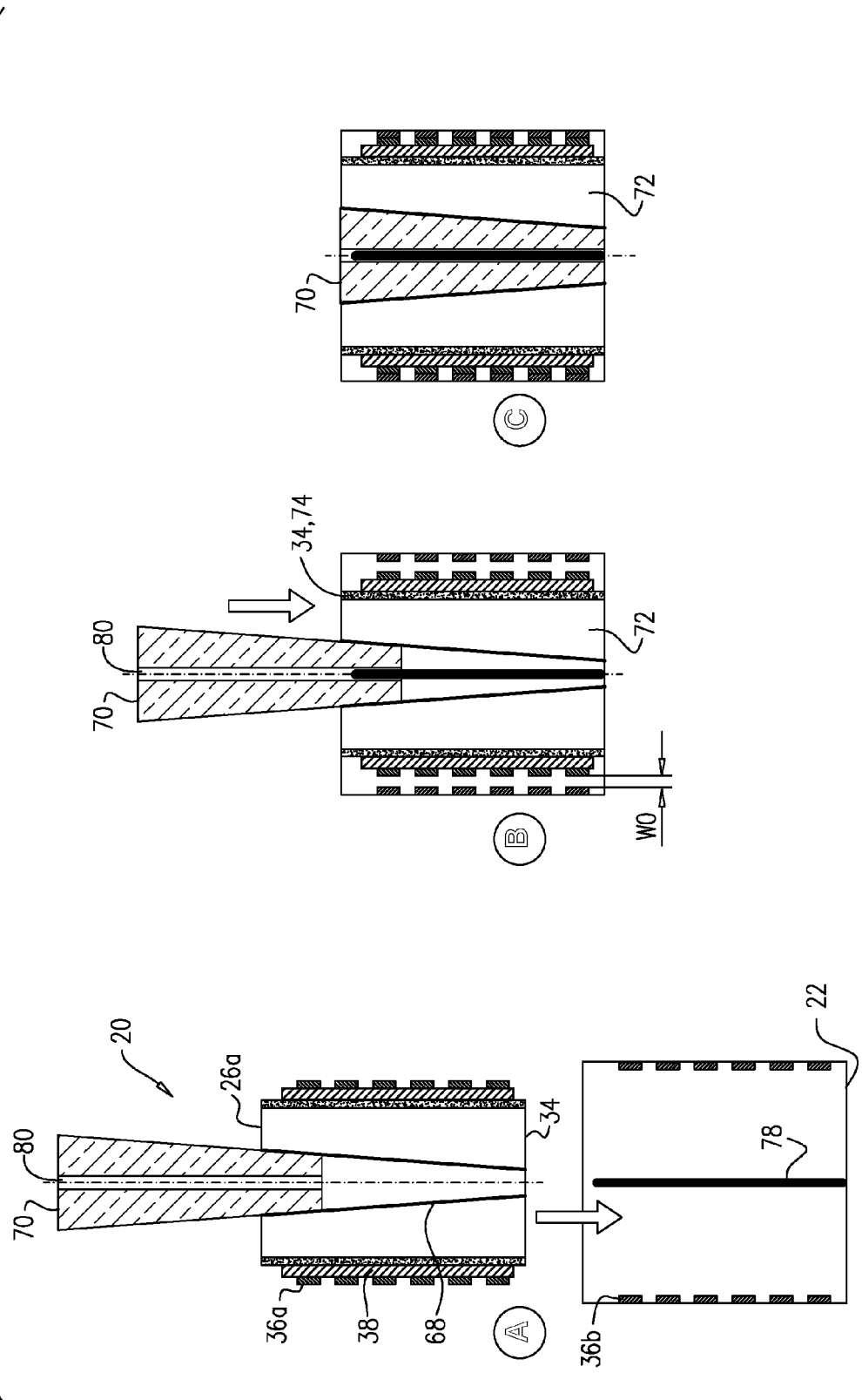

Reference is first made to FIGS. 6A-B. FIG. 6A shows a side view of the connectors, while FIG. 6B shows a parallel top view of the connectors.

As in other embodiments described herein, in the embodiment shown in FIGS. 6A-B, a plurality of electrically-conductive male-connector terminals 36a are coupled to mating surface 34 of male-connector body 26a. For example, as shown in the figure, the male-connector terminals may be attached to one or more PCBs 38 on the mating surface. As in other embodiments, the male-connector terminals are coupled to the mating surface in a longitudinal and circumferential arrangement. In other words, the terminals are arranged in an arrangement that is both longitudinal and circumferential. For example, as shown in FIGS. 6A-B, the terminals may be arranged in a plurality of longitudinally-arranged circumferential "rings." Such an arrangement effectively covers a large portion of the mating surface, such that male connector 20 may comprise a relatively large number of terminals.

Unlike other embodiments described above, however, the mating surface does not necessarily narrow toward the distal end thereof. For example, in some embodiments, rather than being conically-shaped, mating surface 34 is polygonal-prism-shaped (as in FIGS. 6A-B), or cylindrically-shaped.

In the embodiment shown in FIGS. 6A-B, male-connector body 26a is shaped to define a hollow core 68, which is typically narrower (i.e., radially smaller) at the distal end thereof than at the proximal end thereof. A longitudinal insert 70 is provided. The shape of longitudinal insert 70 typically complements the shape of core 68, in that (i) the distal end of the longitudinal insert is narrower than the proximal end of longitudinal insert, and (ii) the shape of the cross-section of the longitudinal insert matches that of the core. For example, as shown in FIG. 6A-B, core 68 may have a polygonal cross-section, and the longitudinal insert may therefore, complementarily, be pyramidally-shaped. (In other words, the proximal end of the longitudinal insert may be shaped to define a polygonal base, and each side of the longitudinal insert may be shaped to define at least part of a triangle that extends distally, and radially inward, from the base.) Alternatively, core 68 may have a circular cross-section, and the longitudinal insert may therefore, complementarily, be conically-shaped. (In general, the shape of the core and longitudinal insert is independent of the shape of the mating surface of the male connector.)

The longitudinal insert is typically somewhat wider (i.e., radially larger) than the core, such that the longitudinal insert expands the core upon being inserted into the core, as further described below.

In step A of FIGS. 6A-B, male-connector body 26a is inserted into female connector 22. Upon full insertion of male-connector body 26a, as depicted in step B, each of the male-connector terminals is aligned with its respective complementary female-connector terminal. The width of the male-connector body is small enough, relative to that of the female connector, such that it is relatively unlikely that the male-connector terminals will contact any of the female-connector terminals during the insertion. For example, as depicted in step B, upon insertion of the male-connector body, there may be a gap W0 of at least one mm between each of the male-connector terminals and its nearest female-connector terminal.

In step B, the longitudinal insert is moved distally inside core 68 (i.e., the longitudinal insert is inserted further into core 68). Due to the greater width of the longitudinal insert relative to the core, the distal movement of the longitudinal insert within the core expands the core, thus pushing the male-connector terminals radially outward, toward the female-connector terminals. Finally (step C), upon completion of the insertion of the longitudinal insert, contact is established between the male-connector terminals and the female-connector terminals, such that each one of the male-connector terminals is in contact with a respective one of the female-connector terminals.

Typically, mating surface 34 of the male connector, upon which the PCBs and/or terminals are disposed, comprises an elastic material 74, comprising, for example, rubber. In such embodiments, the distal movement of the longitudinal insert stretches—and in particular, circumferentially expands—the elastic material, thus facilitating the pushing of the male-connector terminals toward the female-connector terminals. (In step C in FIG. 6B, the corners of the elastic material are drawn differently from the rest of the elastic material, to indicate that these portions of the elastic material are stretched.)

In some embodiments, as shown in FIGS. 6A-B, the longitudinal insert does not push directly against the mating surface, but rather, pushes against a (typically electrically-insulative) material 72 disposed between the core and the mating surface. Material 72 may comprise, for example, a plurality of sections, which become separated from each other, in tandem with the expansion of the elastic material, as the longitudinal insert is inserted into the core. (The separation of the sections is shown in step C of FIG. 6B.)

In some embodiments, the female connector comprises a longitudinal protrusion 78, and the longitudinal insert is shaped to define a hollow insert-core 80 shaped to fittingly receive protrusion 78. In such embodiments, as shown in step A in FIG. 6A, the longitudinal insert is typically partially inserted into the male-connector body prior to the insertion of the male-connector body into the female connector. Subsequently, the male-connector body is aligned with the female connector by aligning the protrusion with insert-core 80. Thus, protrusion 78 helps prevent unwanted contact between the terminals as the male-connector body is inserted into the female connector. For example, if (i) protrusion 78 is at the center of the female connector, as shown, (ii) insert-core 80 is at the center of the male-connector body, as shown, and (iii) the (outer) width of the male-connector body is smaller than the (inner) width of the female connector, as described above, unwanted contact between the terminals will be entirely prevented.

Reference is now made to FIGS. 7A-B. FIG. 7A shows a side view of the connectors, while FIG. 7B shows a parallel top view of the connectors.

In the embodiment shown in FIGS. 7A-B, longitudinal insert 70 radially pushes the male-connector terminals outward, toward the female-connector terminals, by rotating inside core 68. In particular, in step A, the male-connector body, with the longitudinal insert fully inserted into core 68, is inserted into the female connector. As in FIGS. 6A-B, the prevention of unwanted contact between the terminals is facilitated by the male-connector body being sufficiently narrower (i.e., radially smaller) than the inner surface of the female-connector body, and/or by protrusion 78.

Following the complete insertion of the male-connector body, the longitudinal insert is rotated about its longitudinal axis inside core 68 (step B). As shown in step C, the rotation of the longitudinal insert pushes the male-connector terminals outward. (Alternatively or additionally, to push the male-connector terminals radially outward, the male-connector body may be rotated with respect to the longitudinal insert in the opposite direction.) Typically, in such "rotation-based" embodiments, the longitudinal insert is polygonal-prism-shaped. As the longitudinal insert is rotated, the corners of the longitudinal insert push the sections of material 72 radially outward, thus stretching the elastic material and pushing the terminals radially outward, as described above with reference to FIGS. 6A-B.

In general, the scope of the present invention includes radially pushing the male-connector terminals by any type of movement of the longitudinal insert inside the hollow core of the male connector. Examples of relevant types of movement include distal movement (as in FIGS. 6A-B), rotation (as in FIGS. 7A-B), and a combination of distal movement and rotation.

Figure 8B:
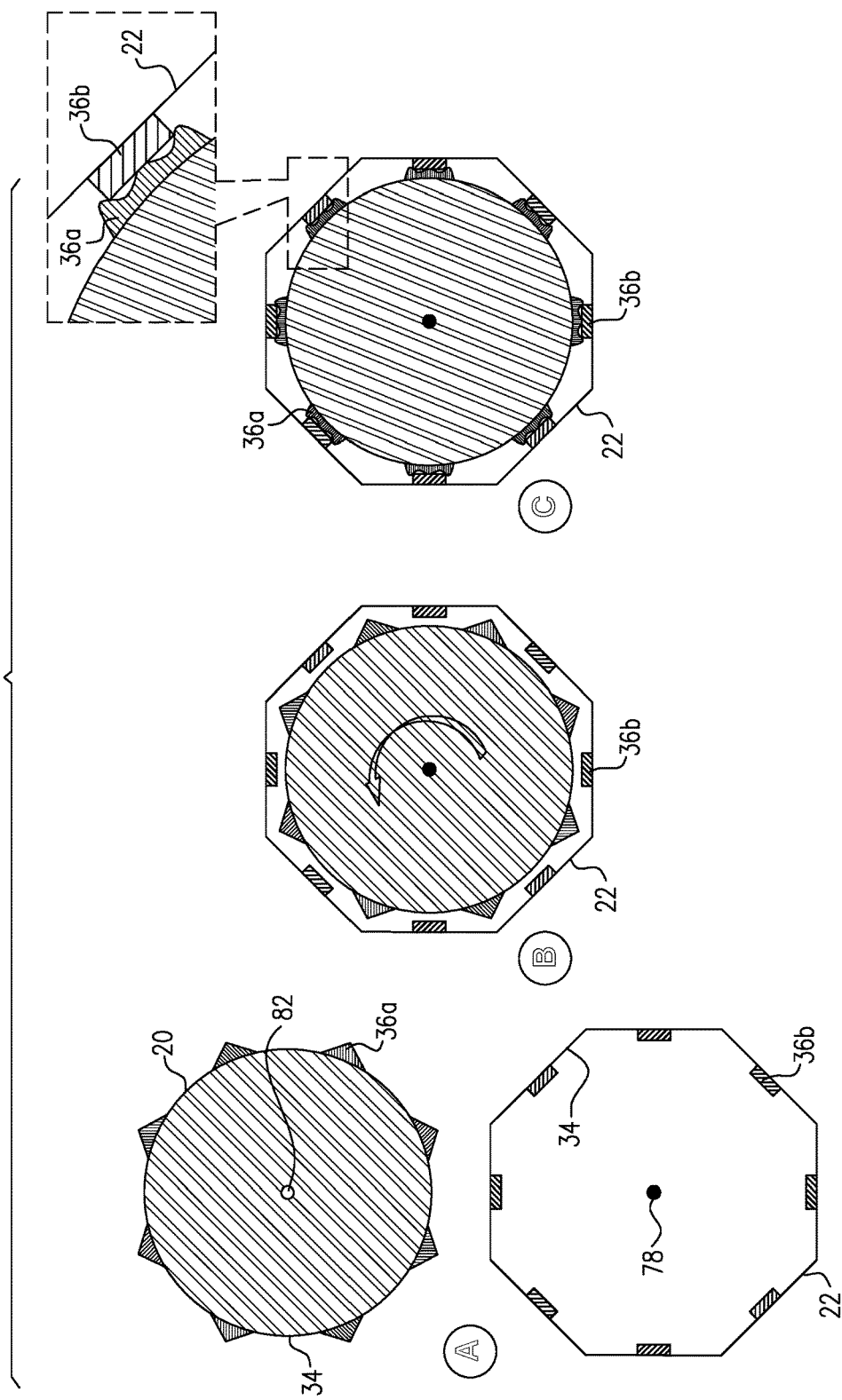

Reference is now made to FIGS. 8A-B. FIG. 8A shows a side view of the connectors, while FIG. 8B shows a parallel top view of the connectors.

In the embodiment of FIGS. 8A-B, the male connector and female connector are shaped such that the two sets of terminals are misaligned with one another upon insertion of the male connector. Only subsequently, during the second mating step, upon rotation of the male connector (or at least the male-connector body), are the terminals brought into contact.

As in previously-presented embodiments, male connector 20 comprises a male-connector body, comprising at least one mating surface 34, and a plurality of electrically-conductive male-connector terminals coupled to the mating surface of the male-connector body. Typically, the male-connector terminals are coupled to the mating surface in a longitudinal and circumferential arrangement, such as to effectively utilize the surface area provided by the male-connector body.

In step A, the male-connector body is inserted into the female connector, such that no one of the male-connector terminals is in contact with any one of the female-connector terminals. Subsequently, in step B, the male-connector body and female connector are rotated with respect to one another, such as by rotating the male-connector body while holding the female connector in place (as illustrated in FIG. 8B), or vice versa, or by rotating both of the connectors, at the same time, in opposite directions. The rotation brings each one of the male-connector terminals into contact with a respective one of the female-connector terminals.

Typically, the male-connector terminals are radially movable with respect to the male-connector body. For example, the male-connector terminals may be compressible, and/or may be disposed on compressible springs attached to the male-connector body. As shown in FIG. 8B, the radial movability of the male-connector terminals facilitates contact between the respective sets of terminals.

In some embodiments, to facilitate the insertion, the male-connector body is shaped to define a hollow core 82, which is shaped to fittingly receive a protrusion 78 that protrudes from the bottom inside surface of the female-connector body. (Core 82 thus behaves analogously to insert-core 80 of FIGS. 6-7.) Alternatively or additionally, to further help prevent unwanted contact between the terminals, mating surface 34 of the female connector may comprise a plurality of electrically-insulative protrusions 86 that longitudinally separate between the female-connector terminals. For example, circumferential protrusions 86 may separate between circumferential rings of female-connector terminals. (Protrusions 86 thus behave analogously to sheath 62 of FIG. 5.)

In some embodiments, to help prevent premature rotation of the male-connector body, the outside surface of one of the connectors is shaped to define a longitudinal track, and the outside surface of the other one of the connectors is shaped to define a protrusion that fits inside the track. As the male-connector body is inserted into the female connector, the protrusion advances along the track. Since, at this point, the track allows only longitudinal movement (and not circumferential movement) of the protrusion, premature rotation of the male-connector body is prevented. At the end of the track, the track turns by 90 degrees, i.e., the track includes a circumferentially-oriented portion. Upon full insertion of the male-connector body, the protrusion reaches the turn in the track, and hence, rotation of the male-connector body is possible. A similar mechanism may be used to help guide the rotation of the longitudinal insert within hollow core 68 (FIGS. 7A-B).

It is noted that the connectors described herein may be used for any suitable medical or non-medical application, and not only in the catheter-based application described herein. For example, the connectors described herein may be used for ultrasound transducers, or for any relevant communication application in which a relatively large number of communication signals are received. Furthermore, the connectors are not necessarily cable-to-cable connectors; for example, the connectors may be cable-to-chassis connectors, cable-to-panel connectors, or daughterboard-to-motherboard connectors.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. Apparatus, comprising:
a connector body comprising at least one mating surface having a first longitudinal end, and a second longitudinal end that is narrower than the first longitudinal end;
a plurality of electrically-conductive terminals coupled to the mating surface of the connector body;
wherein the mating surface is an inner surface of the connector body, such that the connector body is a female-connector body; and
wherein the female-connector body is shaped to define at least one protrusion that protrudes from the second longitudinal end of the female-connector body toward the first longitudinal end of the female-connector body, the protrusion not being at a transverse center of the female-connector body.

2. The apparatus according to claim 1, further comprising a catheter, the connector body being disposed at a proximal end of the catheter.

3. The apparatus according to claim 2, wherein the catheter comprises a plurality of electrodes at a distal end thereof, each of the electrodes at the distal end of the catheter being connected to a respective one of the terminals.

4. The apparatus according to claim 1, further comprising:
an electrically-insulative layer of material covering the inner surface of the connector body and shaped to define a plurality of apertures positioned such that each one of the apertures is aligned with a respective one of the electrically-conductive terminals; and
a plurality of electrical conductors disposed, respectively, within the apertures.

5. Apparatus, comprising:
a connector body comprising at least one mating surface having a first longitudinal end, and a second longitudinal end that narrower than the first longitudinal end;
a plurality of electrically-conductive terminals coupled to the mating surface of the connector body;
wherein the mating surface is an outer surface of the connector body, such that the connector body is a male-connector body, and the terminals are male-connector terminals; and
wherein the second longitudinal end of the male-connector body is shaped to define at least one orifice that is not at a transverse center of the male-connector body.

6. The apparatus according to claim 1, further comprising:
an electrically-insulative connector sheath, shaped to define a plurality of apertures positioned such that, when one of the connector body and connector sheath is inside the other one of the connector body and connector sheath, each one of the apertures is aligned with a respective one of the electrically-conductive terminals; and
a plurality of electrical conductors disposed, respectively, within the apertures.

7. The apparatus according to claim 5, further comprising a female connector, comprising:
a female-connector body shaped to fittingly receive the male-connector body and the male-connector terminals, and
a plurality of electrically-conductive female-connector terminals coupled to an inner surface of the female-connector body, each of the female-connector terminals being positioned to contact a respective one of the male-connector terminals when the male-connector terminals are inside the female connector.

8. Apparatus, comprising:
a connector body comprising at least one mating surface having a first longitudinal end, and a second longitudinal end that is narrower than the first longitudinal end;
a plurality of electrically-conductive terminals coupled to the mating surface of the connector body;
wherein the terminals are terminals of one or more printed circuit boards (PCBs) coupled to the mating surface; and
wherein the PCBs comprise, between at least one pair of the terminals, a spacing element that is level with the pair of terminals.

9. The apparatus according to claim 6, wherein the plurality of electrical conductors comprise a plurality of electrically-conductive balls.

10. The apparatus according to claim 1, wherein the mating surface is conically-shaped.

11. The apparatus according to claim 1, wherein the electrically-conductive terminals consist of 100-500 terminals.

12. The apparatus according to claim 1, further comprising a compressible layer of material between at least a portion of the connector body and the terminals.

13. The apparatus according to claim 1, wherein the apparatus is shaped to define one or more ridges configured to facilitate a fastening of the apparatus to a complementary connector in a mating position, by receiving one or more fasteners of the complementary connector.

14. The apparatus according to claim 1, wherein the apparatus further comprises one or more fasteners configured to fasten the apparatus to a complementary connector in a mating position.

15. The apparatus according to claim 14, wherein the fasteners comprise one or more tabs.

16. The apparatus according to claim 14, wherein the fasteners comprise one or more magnets.

* * * * *